United States Patent
Ooshio et al.

(10) Patent No.: US 11,925,646 B2
(45) Date of Patent: Mar. 12, 2024

(54) AGENT FOR TREATING OR PREVENTING CANCER, AND COMBINATION OF RF PATHWAY INHIBITOR AND MEK INHIBITOR FOR TREATING OR PREVENTING CANCER

(71) Applicants: NATIONAL UNIVERSITY CORPORATION HOKKAIDO UNIVERSITY, Sapporo (JP); Tsuzuki Educational Institute, Fukuoka (JP)

(72) Inventors: Takako Ooshio, Sapporo (JP); Masahiro Sonoshita, Sapporo (JP); Satoshi Ichikawa, Sapporo (JP); Yusuke Satoh, Sapporo (JP); Kiyonaga Fujii, Fukuoka (JP)

(73) Assignees: NATIONAL UNIVERSITY CORP. HOKKAIDO UNIVERSITY, Sapporo (JP); Tsuzuki Educational Institute, Fukuoka (JP)

( * ) Notice: Subject to any disclaimer, the term of this patent is extended or adjusted under 35 U.S.C. 154(b) by 0 days.

(21) Appl. No.: 17/680,972

(22) Filed: Feb. 25, 2022

(65) Prior Publication Data
US 2022/0280521 A1    Sep. 8, 2022

(30) Foreign Application Priority Data
Feb. 26, 2021    (JP) ................. 2021-029585

(51) Int. Cl.
*A61K 31/525*    (2006.01)
*A61P 35/00*    (2006.01)

(52) U.S. Cl.
CPC ............ *A61K 31/525* (2013.01); *A61P 35/00* (2018.01)

(58) Field of Classification Search
CPC ............................. A61K 31/525; A61P 35/00
See application file for complete search history.

(56) References Cited

U.S. PATENT DOCUMENTS 9,402,849 B2 *  8/2016  Matuschka-Greiffenclau ............. A61K 31/445

OTHER PUBLICATIONS

Mack et al., Appl Microbol Biotech (2006) 71: 265-275. (Year: 2006).*
Infante et al., Lancet Oncol (2012)13: 773-81 (Year: 2012).*
Kasuga et al., Invest New Drugs (2015) 33: 1058-1067. (Year: 2015).*
Suwannasom et al., Int.J.Mol.Sci. (2020) 2:1-22. (Year: 2020).*
Hertz et al., J Int Med Res 2009, vol. 37, pp. 1961-1971. (Year: 2009).*

* cited by examiner

*Primary Examiner* — Craig D Ricci
*Assistant Examiner* — Janet L Coppins
(74) *Attorney, Agent, or Firm* — MagStone Law, LLP; Enshan Hong (57) ABSTRACT

The present invention provides a method for treatment or prevention of cancer through novel action mechanism, namely, through inhibition of a riboflavin pathway. The method for treatment or prevention of cancer comprises administering an RF pathway inhibitor to a subject in need thereof.

4 Claims, 5 Drawing Sheets
Specification includes a Sequence Listing.

AGENT FOR TREATING OR PREVENTING CANCER, AND COMBINATION OF RF PATHWAY INHIBITOR AND MEK INHIBITOR FOR TREATING OR PREVENTING CANCER

CROSS-REFERENCE TO RELATED APPLICATIONS

The present application claims priority from Japan Patent Application No. 2021-029585 filed on Feb. 26, 2021, the entirety of which is incorporated herein as reference.

SEQUENCE LISTING

The instant application contains a Sequence Listing which has been submitted electronically in ASCII format and is hereby incorporated by reference in its entirety. Said ASCII copy, created on Feb. 25, 2022, is named Sequence.txt and is 1,269 bytes in size.

TECHNICAL FIELD

The present invention relates to a method for treatment or prevention of cancer.

BACKGROUND OF THE INVENTION

Pancreatic cancer is a representative intractable cancer that is difficult to detect at an early stage, and has substantially no effective treatment. It is presumed that the number of pancreatic cancer deaths will definitely increase over the world in the future, and elucidation of the onset mechanism and development of a novel treatment are urgent welfare problems (Non Patent Literature 1).

Regarding pancreatic cancer, activating mutation in cancer gene KRAS and inactivating mutation in tumor suppressor genes TP53, P16 and SMAD4 are observed respectively in 40 to 90% of the patients, and a group of patients having the poorest prognosis has the mutations in all of these four genes (Non Patent Literatures 2 and 3).

Riboflavin is a physiologically active substance also designated as vitamin B2, and classified into water soluble vitamins. A mammal cannot produce riboflavin in the body, and hence needs to ingest it as food or the like, and the deficiency thereof causes growth stop, keratitis, dermatitis, stomatitis and the like. There are various analogs of riboflavin, and roseoflavin, that is, one of the riboflavin analogs, is known as an antimicrobial (Non Patent Literature 4).

CITATION LIST

Non Patent Literature

[Non Patent Literature 1] Rahib et al., Cancer Res. 2014 Jun. 1; 74(11): 2913-21
[Non Patent Literature 2] Qian et al., JAMA Oncol. 2018; 4(3): e173420
[Non Patent Literature 3] Makohon-Moore et al., Nat Rev Cancer, 2016 September; 16(9): 553-65
[Non Patent Literature 4] Pedrolli et al., Biochem Pharmacol. 2011 Dec. 15; 82(12): 1853-9

SUMMARY OF INVENTION

Technical Problem

Cancer mortality and cancer incidence have been both increasing mainly because of the aging of population, and development of an effective treatment for intractable cancer having a poor prognosis such as pancreatic cancer has been awaited.

The present invention was devised in consideration of the above-described circumstances, and an object is to provide a method for treatment or prevention of cancer through novel action mechanism, namely, through inhibition of a riboflavin pathway.

Solution to Problem

For achieving the above-described object, a method for treatment or prevention of cancer according to a first aspect of the present invention comprises administering an RF pathway inhibitor.

The cancer is, for example, pancreatic cancer.
The RF pathway inhibitor is, for example, roseoflavin.
The method further comprises, for example, administering a MEK inhibitor.
The MEK inhibitor is, for example, trametinib.

A method for treatment or prevention of cancer according to a second aspect of the present invention comprises administering a combination of an RF pathway inhibitor and a MEK inhibitor.

The cancer is, for example, pancreatic cancer.
The RF pathway inhibitor is, for example, roseoflavin.
The MEK inhibitor is, for example, trametinib.

Advantageous Effect of Invention

According to the present invention, a method for treatment or prevention of cancer through novel action mechanism, namely, through inhibition of a riboflavin pathway.

BRIEF DESCRIPTION OF DRAWINGS

FIG. 5 illustrates graphs of influence on a relative survival rate of roseoflavin in cultured human pancreatic cancer cell lines, in which FIG. 5(a) is obtained using MIAPaCa-2, FIG. 5(b) is obtained using PANC-1, and FIG. 5(c) is obtained using Capan-1.

FIG. 7 illustrates graphs of suppression of spheroid formation in cultured human pancreatic cancer cell line (AsPC-1) through use of both roseoflavin and trametinib, wherein FIG. 7(a) is a photograph of each group on day 21 of culture, and FIG. 7(b) is a graph of the number of spheroids measured for each size in each group on day 21 of culture.

FIG. 8 illustrates graphs of suppression of spheroid formation in cultured human pancreatic cancer cell line (Capan-1) through use of both roseoflavin and trametinib, wherein FIG. 8(a) is a photograph of each group on day 21 of culture, and FIG. 8(b) is a graph of the number of spheroids measured for each size in each group on day 21 of culture.

DETAILED DESCRIPTION OF PREFERRED EMBODIMENTS OF THE INVENTION (1. Method for Treatment or Prevention of Cancer)

A method for treatment or prevention of cancer comprises administering an RF pathway inhibitor.

Herein, the term "treatment of cancer" embraces medically acceptable therapeutic intervention for various purposes including delay or stop of cancer progression, remission or temporary remission of cancer, regression or elimination of cancerous lesions, growth inhibition of cancer cells, prevention of cancer recurrence, and the like. Besides, the term "agent for treating cancer" refers to an agent for delaying or stopping cancer progression, an agent for remitting or temporarily remitting cancer, an agent for regressing or eliminating cancerous lesions, an agent for inhibiting growth of a cancer cells, an agent for preventing cancer recurrence, and the like.

Herein, the term "prevention of cancer" embraces medically acceptable preventive intervention for various purposes including prevention of onset or incidence of cancer, prevention of formation of cancerous lesions, prevention of occurrence of precancerous condition, and the like. Besides, the term "agent for preventing cancer" refers to an agent for preventing onset or incidence of cancer, an agent for preventing formation of cancerous lesions, an agent for preventing occurrence of precancerous condition, and the like.

Herein, examples of the "cancer" include, but are not limited to, pancreatic cancer, leukemia (such as acute myelogenous leukemia, chronic myelogenous leukemia, acute lymphoid leukemia, or chronic lymphoid leukemia), malignant lymphoma (Hodgkin's lymphoma, or non-Hodgkin's lymphoma (such as adult T-cell leukemia, follicular lymphoma, or diffuse large B-cell lymphoma)), multiple myeloma, myelodysplastic syndromes, head and neck carcinoma, gastrointestinal carcinoma (such as esophageal carcinoma, esophageal adenocarcinoma, gastric carcinoma, colorectal carcinoma, colon carcinoma, or rectal carcinoma), liver carcinoma (such as hepatocellular carcinoma), gallbladder/bile duct carcinoma, biliary tract cancer, thyroid carcinoma, lung carcinoma (such as non-small cell lung carcinoma (such as squamous non-small cell lung carcinoma, or non-squamous non-small cell lung carcinoma), or small cell lung carcinoma), breast carcinoma, genitourinary carcinoma (such as ovarian carcinoma (such as serous ovarian carcinoma), cervical carcinoma, uterine body carcinoma, endometrial carcinoma, vaginal carcinoma, vulvar carcinoma, kidney carcinoma (such as renal cell carcinoma), urothelial carcinoma (such as bladder carcinoma, or upper urinary tract carcinoma), prostate carcinoma, testicular carcinoma (such as term cell tumor), bone and soft tissue tumor, skin carcinoma (such as uveal malignant melanoma, melanoma, or Merkel cell carcinoma), glioma, brain tumor (such as glioblastoma), pleural mesothelioma, and carcinoma of unknown primary. Cancer is preferably pancreatic cancer. Examples of pancreatic cancer include exocrine tumor, such as invasive ductal cancer, pancreatic acinar cell cancer, or intraductal papillary mucinous neoplasm, and endocrine tumor, such as neuroendocrine tumor.

Herein, an RF pathway refers to RF (riboflavin) metabolic pathway. RF is a nutrient (alias: vitamin B2) contained in food, and is incorporated into a cell via an RFT (RF transporter) locally present in the cell membrane to be changed to FMN (flavin mononucleotide) through phosphorylation by RFK (RF kinase). RFK is a rate limiting enzyme for RF metabolism. FMN is further converted into FAD (flavin adenine dinucleotide) by FLAD1 (FAD synthetase 1). FMN and FAD bind to various flavoproteins as a coenzyme to regulate various metabolic reactions significant for producing energy and maintaining homeostasis as in a redox reaction (Lienhart et al., Arch Biochem Biophys. 2013 Jul. 15; 535(2): 150-62).

Herein, the term "RF pathway inhibitor" means an agent for inhibiting an RF pathway through action on one or more substances involved in the RF pathway. Accordingly, the RF pathway inhibitor may act on any one of RF, RFT, RFK, FMN, FLAD1, and FAD, and may act on another substance different from these to inhibit the RF pathway. In other words, the form of "inhibiting" an RF pathway by the "RF pathway inhibitor" is not especially limited, and may be, for example, (i) by competing with RF, (ii) by directly inhibiting the function of RFT, RFK, FMN, FLAD1 or FAD, or (iii) by indirectly inhibiting the RF pathway by capturing a substance necessary for a substance present in the RF pathway and different from those described above.

The "RF pathway inhibitor" is, for example, an RF analog (riboflavin analog). Herein, the term "RF analog" refers to a compound having a similar structure to riboflavin, obtained by replacing a part of atoms or functional groups of riboflavin with another atom or functional group, and having an RF pathway inhibitory effect. Examples of the RF analog include roseoflavin and T308471. The RF analog is preferably roseoflavin.

The agent for treating or preventing cancer according to the present invention may contain, in addition to the RF pathway inhibitor, a MEK inhibitor as an active ingredient.

MEK (MAPK (mitogen activated protein kinase)/ERK (extracellular signal regulated kinase) kinase) is one of the protein kinases constituting a MAPK cascade. A MAPK cascade forms a complicated signal transduction network for controlling a variety of cellular processes such as cell proliferation, growth, differentiation and apoptosis. When MEK is inhibited, cell proliferation is stopped to induce apoptosis, and hence, MEK attracts attention as a target molecule of an anticancer agent, and various MEK inhibitors have been reported.

Examples of the MEK inhibitor used in the present invention includes trametinib, cobimetinib, binimetinib, selumetinib, pimasertib, mirdametinib, refametinib, PD184352, PD98059, BIX02189, BIX02188, TAK-733, AZD8330, PD318088, myricetin, BI-847325, GDC-0623, Ro5126766, PD334581, PD198306, RO4987655, and HI TOPK 032. The MEK inhibitor is preferably trametinib.

When the agent for treating or preventing cancer according to the present invention contains, as an active ingredient, the MEK inhibitor in addition to the RF pathway inhibitor, each of the RF pathway inhibitor and the MEK inhibitor is not limited to one compound. For example, these inhibitors are not limited to a combination of one RF pathway inhibitor and one MEK inhibitor but embrace a combination of one RF pathway inhibitor and two or more MEK inhibitors, a combination of two or more RF pathway inhibitors and one MEK inhibitor, and a combination of two or more RF pathway inhibitors and two or more MEK inhibitors.

When the agent for treating or preventing cancer according to the present invention contains, as an active ingredient, the MEK inhibitor in addition to the RF pathway inhibitor, the RF pathway inhibitor is preferably roseoflavin, and the MEK inhibitor is preferably trametinib.

When the agent for treating or preventing cancer according to the present invention contains, as an active ingredient, the MEK inhibitor in addition to the RF pathway inhibitor, the agent may be in the form of a formulation containing both the RF pathway inhibitor and the MEK inhibitor, or may be in the form of a combination of separate formulations of these. When it is in the form of the combination of separate formulations of the RF pathway inhibitor and the MEK inhibitor, the order and the time of administration of the respective formulations are not especially limited, and these may be simultaneously administered, or may be administered at an interval at different times or on different days.

The agent for treating or preventing cancer according to the present invention is administered to a subject affected by cancer, such as rodents including a mouse, a rat, a hamster, and a guinea pig, primates including a human, a chimpanzee, and a rhesus monkey, domestic animals including a pig, a cow, a goat, a horse and a sheep, and pets including a dog and a cat. The subject is preferably a human.

A method for administering the agent for treating or preventing cancer according to the present invention can be appropriately selected from oral administration, topical administration, intravenous administration, intraperitoneal administration, intradermal administration, sublingual administration and the like. A dosage form for the administration may be optional, and can be appropriately prepared in the form of, for example, an oral solid preparation such as a tablet, a granule, a powder, or a capsule, an oral liquid preparation such as an internal liquid or a syrup, or a parenteral liquid preparation such as an injection. Besides, an appropriate drug delivery system (DDS) may be used. Such a dosage form can be produced by formulating active ingredients by an ordinary method. In addition, various medically acceptable substances for formulation can be compounded if necessary in the formulation. The substances for formulation can be appropriately selected depending on the dosage form of the formulation, and examples include a buffer, a surfactant, a stabilizer, a preservative, an excipient, a diluent, an additive, a disintegrating agent, a binder, a coating agent, a lubricant, a lubricating agent, a flavor, a sweetener, and a solubilizing agent.

A dose and the number of doses of the agent for treating or preventing cancer according to the present invention can be appropriately set by those skilled in the art depending on the type of cancer, a health condition, the age, and the weight of a patient, an administration route and a dosage form to be employed, and the like, so that an effective amount can be administered to the patient.

(2. Combination)

A method for treatment or prevention of cancer comprises administering a combination of an RF pathway inhibitor and a MEK inhibitor.

The details of the respective terms "cancer", "treatment", "prevention", "RF pathway inhibitor" and "MEK inhibitor" are the same as those described above.

Cancer to which the combination of the present invention is applied is preferably pancreatic cancer. Examples of pancreatic cancer include exocrine pancreatic tumor, such as invasive ductal carcinoma, pancreatic acinar cell cancer, or intraductal papillary mucinous neoplasm, and endocrine tumor, such as neuroendocrine tumor.

The RF pathway inhibitor used in the combination of the present invention is preferably roseoflavin.

The MEK inhibitor used in the combination of the present invention is preferably trametinib.

The term "combination" means a combination intended to be administered together or separately, and simultaneously or sequentially to a subject requiring it, namely, a subject desiring cancer treatment. The combination may be in the form of a formulation containing both the RF pathway inhibitor and the MEK inhibitor, or may be in the form of a combination of separate formulations of these. When it is in the form of the combination of separate formulations of the RF pathway inhibitor and the MEK inhibitor, the order and the time of administration of the respective formulations are not especially limited, and these may be simultaneously administered, or may be administered at an interval at different times or on different days.

Each of the RF pathway inhibitor and the MEK inhibitor included in the combination of the present invention is not limited to one compound. For example, the combination is not limited to a combination of one RF pathway inhibitor and one MEK inhibitor, but embraces a combination of one RF pathway inhibitor and two or more MEK inhibitors, a combination of two or more RF pathway inhibitors and one MEK inhibitor, and a combination of two or more RF pathway inhibitors and two or more MEK inhibitors.

In the combination of the present invention, the RF pathway inhibitor is preferably roseoflavin, and the MEK inhibitor is preferably trametinib.

A subject to which the combination of the present invention is applied, a method for administering the combination of the present invention, a dosage form for the administration, a formulation method, a dose, and the number of doses are the same as those described above.

(3. Conclusion)

As described so far, the agent for treating or preventing cancer according to the present invention is an agent containing the RF pathway inhibitor as an active ingredient for treating or preventing cancer such as pancreatic cancer through novel action mechanism. When the MEK inhibitor is used in combination with the RF pathway inhibitor, a more effective agent for treating or preventing cancer can be provided.

Besides, the combination for treating or preventing cancer according to the present invention is a combination of the RF pathway inhibitor and the MEK inhibitor, and can be a novel drug for treating or preventing cancer such as pancreatic cancer.

EXAMPLES

Now, the present invention will be specifically described by way of examples. It is noted that the present invention is not limited to these examples.

Example 1

A *Drosophila* model of a human pancreatic cancer genotype was created as follows.

A genomic DNA was extracted from w$^-$ *Drosophila* (Bloomington *Drosophila* Stock Center) by an ordinary method. This genomic DNA was used as a template to perform PCR using a primer DNA pair designed to amplify Ras85D gene to obtain a DNA fragment containing a nucleotide sequence of Ras85D gene. Besides, a primer DNA for introducing a site-specific mutation for replacing a codon encoding a glycine at 12 position in an amino acid sequence of Ras85D with a codon encoding aspartic acid is designed and synthesized to perform PCR using the DNA fragment as a template, and thus, a DNA fragment encoding Ras85D mutation (Ras$^{G12D}$) was produced. This DNA fragment was inserted into a pWALIUM vector (Harvard Medical School), that is, a knockdown vector for a *Drosophila*, to produce a pWALIUM. UAS-RasG12D vector. This vector was microinjected into a *Drosophila* y$^1$w$^{67c23}$; P{CaryP}attP2 to create a UAS-RasG12D fly in which a DNA encoding RasG12D was inserted into the L region of the 3rd chromosome by homologous recombination.

Besides, a DNA fragment containing a p53 gene knockdown sequence (sequence containing a sense chain TGCTGAAGCAATAACCACCGA (SEQ ID NO: 1), a hairpin loop TAGTTATATTCAAGCATA (SEQ ID NO: 5), and antisense chain TCGGTGGTTATTGCTTCAGCA (SEQ ID NO: 2) linked to one another) was inserted, together with the DNA fragment encoding RasG12D, into the pWALIUM vector to produce a pWALIUM. UAS-RasG12D, UAS-p53 shRNA vector. This vector was similarly microinjected into a *Drosophila* y$^1$w$^{67c23}$; P{CaryP}attP2 to create a UAS-RasG12D, UAS-p53 shRNA fly in which a DNA encoding RasG12D and shRNA of p53 gene were inserted in the L region of the 3rd chromosome.

Furthermore, a primer DNA pair designed to amplify Cyclin E (CycE) gene was used to perform PCR using the genomic DNA of w⁻ *Drosophila* as a template to obtain a DNA fragment containing a nucleotide sequence of CycE gene. This DNA fragment was inserted into a pWALIUM vector together with a DNA fragment containing a Med gene knockdown sequence (sequence containing a sense chain TTCAGTGCGATGAACATTGCT (SEQ ID NO: 3), a hairpin loop TAGTTATATTCAAGCATA (SEQ ID NO: 5), and an antisense chain AGCAATGTTCATCGCACTGAA (SEQ ID NO: 4) linked to one another) to produce a pWALIUM. UAS-CycE, UAS-Med shRNA vector. This vector was microinjected into a *Drosophila* PBac{yellow[+]-attP-9A}VK00027 to create a UAS-CycE, UAS-Med shRNA fly in which a DNA encoding CycE gene and shRNA of Med gene were inserted in the R region of the 3rd chromosome by homologous recombination.

Subsequently, the UAS-RasG12D, UAS-p53 shRNA fly and the UAS-CycE, UAS-Med shRNA fly were crossbred at 25° C. for 3 days to create UAS-RasG12D, UAS-p53 shRNA, UAS-CycE, UAS-Med shRNA flies.

Each of the UAS-RasG12D, UAS-p53 shRNA, UAS-CycE, UAS-Med shRNA flies was crossbred with a Ser-gal4, UAS-GFP fly (Ser>GFP fly, Bloomington *Drosophila* Stock Center) at 25° C. for 3 days to create Ser>GFP; UAS-RasG12D, UAS-p53 shRNA, UAS-CycE, UAS-Med shRNA flies (referred to as 4-hit flies (Ser>GFP)). In these flies, expression of the introduced genes was induced in localized epithelial cells of a wing disc under control of the Ser promoter (not shown).

The 4-hit flies thus obtained were used in the following tests as a *Drosophila* model of a human pancreatic cancer genotype.

Example 2

A 4-hit fly having heterozygous mutation of riboflavin kinase (RFK) was created to verify influence of RF pathway inhibition on survival rate of 4-hit flies.

Figure 1:
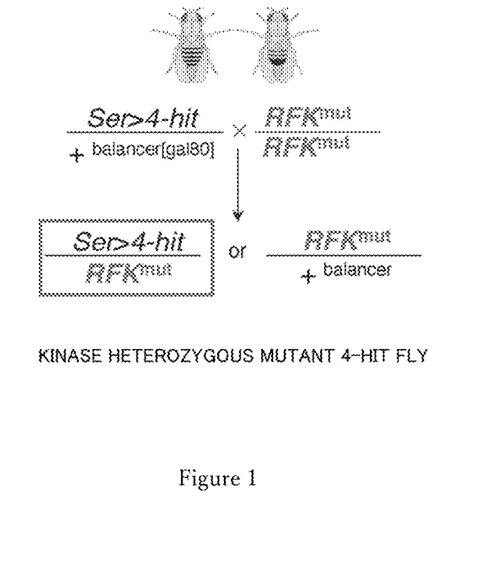
FIG. 1 is a diagram illustrating the outline of a protocol for creating a 4-hit fly carrying a heterozygous mutation for a kinase gene by introducing a heterozygous mutation in a kinase gene into a 4-hit fly.

In accordance with a method of Sonoshita et al., (Curr. Top. Dev. Biol., 2017, 121, 287-309), crossbreed was performed as illustrated in FIG. 1 to verify influence of heterozygous mutation of riboflavin kinase (RFK) on a survival rate of 4-hit flies. Specifically, the UAS-RasG12D, UAS-p53 shRNA, UAS-CycE, UAS-Med shRNA fly in Example 1 was crossbred with a SM5tubgal80-TM6B balancer fly (Dr. Ross Cagan, Icahn School of Medicine at Mount Sinai, NY, USA) to create a UAS-RasG12D, UAS-p53 shRNA, UAS-CycE, UAS-Med shRNA/SM5tubgal80-TM6B fly. Subsequently, this fly was crossbred with a Ser>GFP fly (Bloomington *Drosophila* Stock Center) to create a Ser<GFP; UAS-RasG12D, UAS-p53 shRNA, UAS-CycE, UAS-Med shRNA/SM5tubgal80-TM6B fly.

Besides, from Bloomington *Drosophila* Stock Center (USA), an RFK mutant strain (BDSC No. 30081) was obtained, which was crossbred with the Ser>GFP; UAS-RasG12D, UAS-p53 shRNA, UAS-CycE, UAS-Med shRNA/SM5tubgal80-TM6B fly at 27° C. for 3 days to obtain eggs of a 4-hit fly having RFK heterozygous mutation. As a control, a w⁻ fly was crossbred with the Ser>GFP; UAS-RasG12D, UAS-p53 shRNA, UAS-CycE, UAS-Med shRNA/SM5tubgal80-TM6B fly to obtain eggs of a kinase wild type 4-hit fly. These flies were raised at 27° C. for 13 days, and a survival rate was calculated by dividing the number of eclosed individuals by the total number of pupae.

Figure 2:
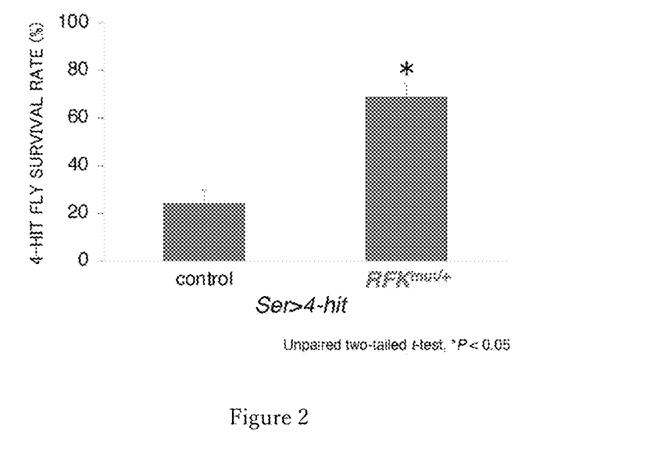
FIG. 2 is a graph illustrating recovery of survival rate of 4-hit flies through introduction of RFK (riboflavin kinase) heterozygous mutation.

Results are illustrated in FIG. 2. It was revealed that lethality was rescued in the 4-hit fly having RFK heterozygous mutation as compared with that of the control. This reveals that the RF pathway inhibition is effective for preventing or treating pancreatic cancer.

Example 3

A 4-hit fly was knocked down for riboflavin (RF) pathway-related genes to verify influence of the RF pathway inhibition on survival rate of 4-hit flies.

As RF metabolic pathway-related genes, riboflavin transporters (RFTs: three types of SLC52A1, SLC52A2, and SLC52A3), riboflavin kinase (RFK), and FAD synthetase (FLAD1) have been reported regarding human genes. On the other hand, regarding fly genes, one type each of RFT and RFK, and CG16848 and FADS as two orthologues of FLAD1 are known.

Figure 3:
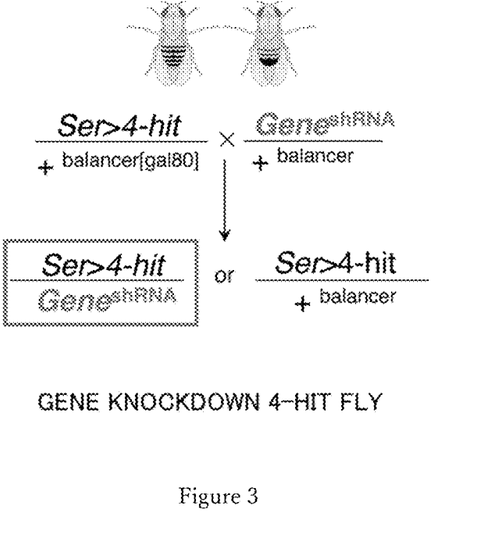
FIG. 3 is a diagram illustrating the outline of a protocol for creating a 4-hit fly in which a specific gene is knocked down.

Crossbreed was performed as illustrated in FIG. 3 to create 4-hit flies by knocking down the following 8 RF pathway-related genes, and influence on survival rate of each of these was verified.

RFT knockdown: KD #1, KD #2
RFK knockdown: KD #1, KD #2
CG16848 knockdown: KD #1, KD #2
FADS knockdown: KD #1, KD #2

Flies necessary for the knockdown were obtained from Bloomington *Drosophila* Stock Center (BDSC, USA), Fly Stocks of National Institute of Genetics (NIG), and Vienna *Drosophila* RNAi Center (VDRC, Austria, Vienna) as follows:

RFT KD #1: BDSC 29531
RFT KD #2: NIG 11576R-3
RFK KD #1: BDSC 57405
RFK KD #2: VDRC 100266
CG16848 KD #1: BDSC 61938
CG16848 KD #2: NIG 16848R-1
FADS KD #1: BDSC 44055
FADS KD #2: NIG 4407R-4

Regarding RFT KD #1, a UAS-RFT (Rift) shRNA/TM3 (BDSC 29531) fly obtained from BDSC was crossbred with a MKRS/TM6B fly to create a UAS-RFT shRNA/TM6B fly. This fly was crossbred with a Ser>GFP; UAS-RasG12D, UAS-p53 shRNA, UAS-CycE, UAS-Med shRNA/

SM5tubgal80-TM6B fly at 27° C. for 2 days to obtain eggs of a 4-hit fly having UAS-RFT shRNA.

Regarding RFT KD #2, RFK KD #1, CG16848 KD #1, and FADS KD #1, flies carrying either of these sequences were crossbred with a FM7C-Tb-RFP/Y (BDSC 36337) fly to create flies of UAS-RFT shRNA/CyO-Tb-RFP, UAS-RFK shRNA/CyO-Tb-RFP, UAS-CG16848 shRNA/CyO-Tb-RFP, and UAS-FADS shRNA/CyO-Tb-RFP.

Regarding FADS KD #2, an FADS KD #2 fly was crossbred with a CyO-Tb-RFP/ap (BDSC 36336) fly to create a fly of UAS-FADS shRNA/CyO-Tb-RFP.

Each of the above-described flies and the flies of RFK KD #2 and CG16848 KD #2 were crossbred with the Ser>GFP; UAS-RasG12D, UAS-p53 shRNA, UAS-CycE, UAS-Med shRNA/SM5tubgal80-TM6B fly at 27° C. for 2 days to obtain eggs of a 4-hit fly having UAS-RF pathway-related gene shRNA.

As a control, a w⁻ fly was crossbred with the Ser>GFP; UAS-RasG12D, UAS-p53 shRNA, UAS-CycE, UAS-Med shRNA/SM5tubgal80-TM6B fly to obtain eggs of a kinase wild type 4-hit fly. These flies were raised at 27° C. for 13 days, and a survival rate was calculated by dividing the number of eclosed individuals by the total number of pupae.

Figure 4:
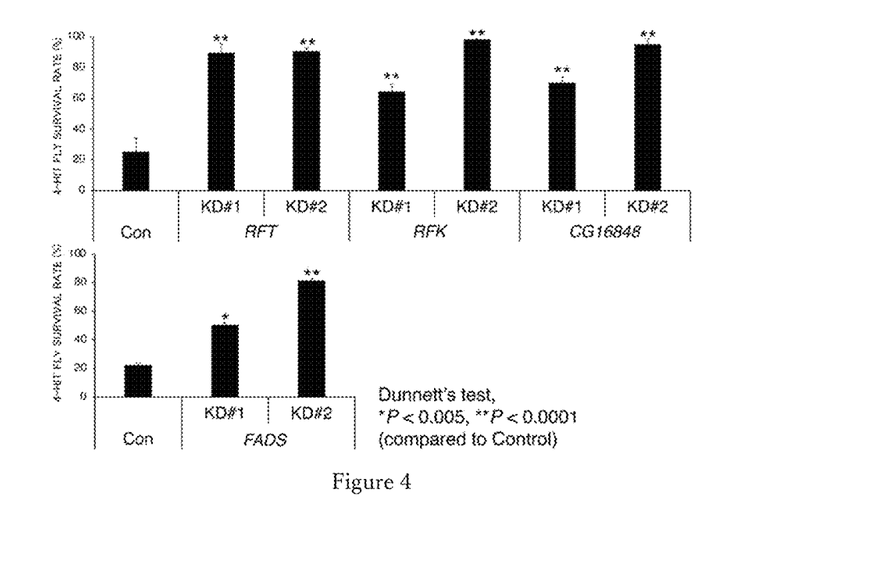
FIG. 4 is a graph illustrating recovery of a survival rate of 4-hit flies through introduction of knockdown of an RF pathway related gene.

Results are illustrated in FIG. 4. It was revealed that the lethality was remarkably rescued in the 4-hit fly having the RF pathway-related gene knockdown as compared with that of the control. This reveals that the RF pathway inhibition is effective for preventing or treating pancreatic cancer.

Example 4

Human pancreatic cancer cells were treated with roseoflavin (RoF), and a relative survival rate was calculated assuming that mitochondrial respiratory chain activity corresponded to the survival rate.

Human pancreatic cancer cell lines, MIAPaCa-2, PANC-1, and Capan-1 were used for performing MTS assay with RoF. All the cell lines were obtained from ATCC. Each of the cell lines was cultured with the following medium in the presence of 5% $CO_2$ at 37° C.

MIAPaCa-2: Dulbecco's Modified Eagle's Medium (Nakalai Tesque) supplemented with 10% fetal bovine serum (Gibco) and 1% penicillin-streptomycin (Nakalai Tesque)

PANC-1: RPMI 1640 medium (Nakalai Tesque) supplemented with 10% fetal bovine serum (Gibco) and 1% penicillin-streptomycin (Nakalai Tesque)

Capan-1: IMDM medium (Iscove's Modified Dulbecco's Medium) (Nakalai Tesque) supplemented with 20% fetal bovine serum (Gibco) and 1% penicillin-streptomycin (Nakalai Tesque)

Roseoflavin (RoF) was prepared to 0 μM (DMSO alone), 0.1 mM, 0.3 mM, 1 mM, 3 mM, and 10 mM, and the resultants were respectively diluted with the medium by 1000 times to obtain agent solutions (RoF final concentration: 0 μM, 0.1 μM, 0.3 μM, 1 μM, 3 μM and 10 M).

In a 96 well plate, MIAPaCa-2 was seeded at 500 cells/well, PANC-1 was seeded at 2,000 cells/well, and Capan-1 was seeded at 10,000 cells/well (in 100 μL of the medium). After these were cultured for 1 day, the RoF agent solution at each concentration was added to the cells in the 96 well plate in an amount of 10 μL each (final concentration of DMSO: 0.1%). Each combination was tested in 3 wells. After the addition of the agent solution, the resultant was cultured in the presence of 5% $CO_2$ at 37° C. for 24, 48 or 72 hours, and a cell survival rate was measured with MTS Assay (Cell Titer 96®, Promega). The survival rate was expressed as a ratio to that of the control (solvent alone) cultured for 72 hours.

Figure 5:
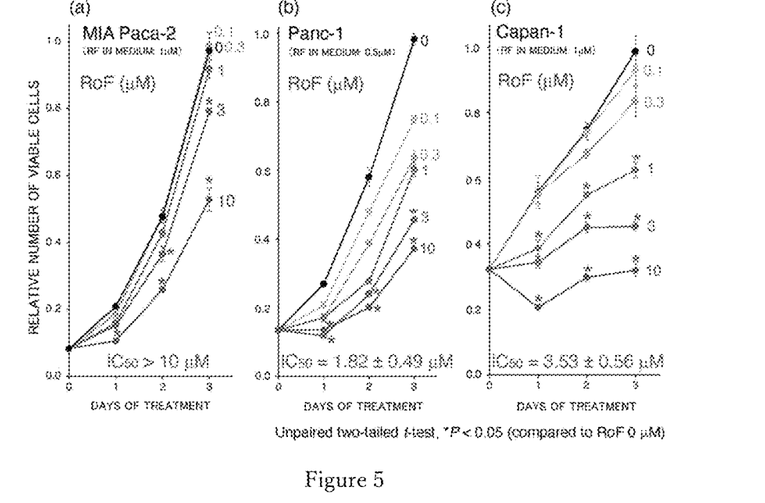

Results are illustrated in FIG. 5. It was revealed that in each human pancreatic cancer cell line, roseoflavin (RoF) deteriorated mitochondrial respiratory chain activity in a dose dependent manner to decrease the relative survival rate. This reveals that the RF pathway inhibitor RoF is effective for preventing or treating pancreatic cancer.

Figure 6:
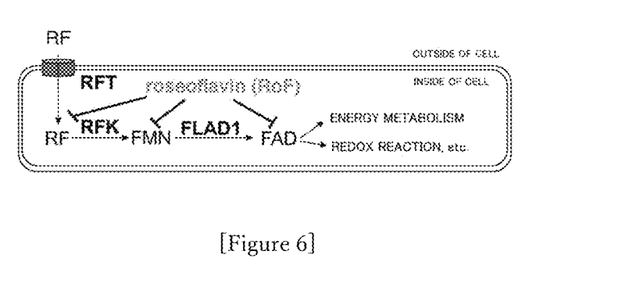
FIG. 6 is a diagram illustrating the outline of RF pathway inhibition by roseoflavin.

The human pancreatic cancer cells (MIAPaCa-2, PANC-1, and Capan-1) treated for 48 hours with 10 μM roseoflavin (RoF) or DMSO (final concentration: 0.1%) as the control were collected to measure, with liquid chromatography mass spectrometry, amounts of RoF, RF (riboflavin), FMN (flavin mononucleotide), and FAD (flavin adenine dinucleotide) within the cells, and thus, it was found that RoF was detected only in the cells treated with RoF, and that the amounts of RF, FMN, and FAD were smaller than those in the control (not shown). Accordingly, it was revealed that RoF suppressed FMN and FAD through competition with RF to inhibit the RF pathway (FIG. 6).

Example 5

A pancreatic cancer suppressing effect through use of both roseoflavin of the RF pathway inhibitor and trametinib of the MEK inhibitor was verified using pancreatic cancer cell lines (AsPC-1 and Capan-1).

The pancreatic cancer cell lines (AsPC-1 and Capan-1) having 4-hit mutation were three-dimensionally cultured in methylcellulose-containing media. Since methylcellulose has a high viscosity and hence cells cannot freely move therein, cells aggregate in the form of aggregation to form a spheroid.

In a 24 well plate (upper layer: 1.8% methylcellulose, lower layer: 0.48% agarose), AsPC-1 was seeded at $5 \times 10^3$ cells/well (in 100 μL of the medium). After culturing for 1 day (day 1), DMSO (control), 10 μM roseoflavin (RoF), 1 nM trametinib (Tr), or 10 μM RoF+1 nM Tr was respectively added to the 24 well plate (final concentration of DMSO: 0.1%). After adding the agent solution, the resultant was cultured in the presence of 5% $CO_2$ at 37° C., and a culture fluid was added on day 14. The resultant was further cultured, and each group was photographed on day 21 to measure the size and the number of spheroids. It is noted that the following media were used for culturing the respective cell lines:

AsPC-1: RPMI 1640 medium (Nakalai Tesque) supplemented with 10% fetal bovine serum (Gibco) and 1% penicillin-streptomycin (Nakalai Tesque)

Capan-1: IMDM medium (Iscove's Modified Dulbecco's Medium) (Nakalai Tesque) supplemented with 20% fetal bovine serum (Gibco) and 1% penicillin-streptomycin (Nakalai Tesque)

Figure 7:
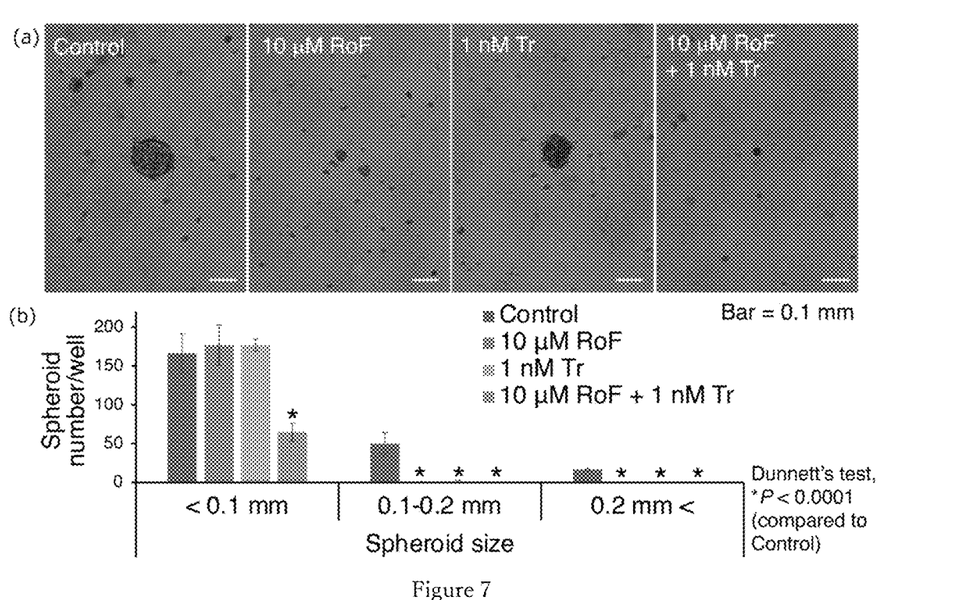
Figure 8:
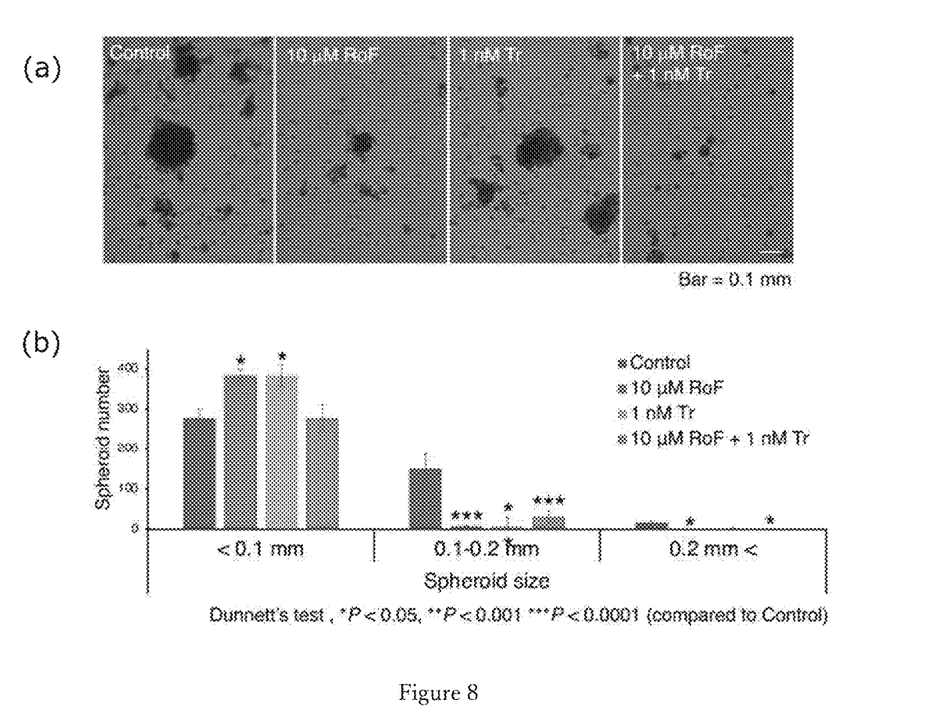

Results obtained in using AsPC-1 are illustrated in FIG. 7, and results obtained in using Capan-1 are illustrated in FIG. 8. In the AsPC-1, regarding spheroids having a size of 0.1 to 0.2 mm and a size larger than 0.2 mm, it was revealed that spheroid formation was suppressed in using roseoflavin (RoF) alone, trametinib (Tr) alone, and both RoF+Tr, and regarding spheroids having a size smaller than 0.1 mm, it was revealed that spheroid formation was further suppressed by using both RoF+Tr (FIG. 7(b)). Also in the Capan-1, regarding spheroids having a size of 0.1 to 0.2 mm and a size larger than 0.2 mm, spheroid formation was suppressed by RoF alone, Tr alone, and both RoF+Tr. On the other hand, when the treatment was performed with RoF alone or Tr alone, the number of spheroids of 0.1 mm or smaller was increased, but when performed with both RoF+Tr, the increase was suppressed, and the total number of spheroids was reduced (FIG. 8(b)). This reveals that use of both trametinib and roseoflavin is very effective for preventing or treating pancreatic cancer.

Example 6

A pancreatic cancer suppressing effect through use of both roseoflavin of the RF pathway inhibitor and trametinib of the MEK inhibitor was verified using a 4-hit fly.

Roseoflavin and trametinib were dissolved in DMSO (Sigma) to be stored at −20° C.

Agar (Wako), brewers' yeast (MPBio), yeast extract (Sigma Aldrich), Bacto Casitone (BD), sucrose (Wako), glucose (Wako), $MgCl_2$ (Wako), $CaCl_2$) (Wako), propionic acid (Wako), Mold Inhibitor (10% methyl-4-hydroxy benzoate in 95% ethanol: Wako) were dissolved in ultrapure water to produce a standard diet. While this was being warmed at 50° C., an agent (trametinib alone, or a combination of roseoflavin and trametinib) dissolved in DMSO was added thereto to be mixed, and the resultant was cooled to prepare an agent diet. Final concentrations in the diet of the respective compounds were set to 0.5 µM for trametinib, and 50 µM for roseoflavin.

The UAS-RasG12D, UAS-p53 shRNA, UAS-CycE, UAS-Med shRNA fly produced in Example 1 was crossbred with a Ser-gal4 fly (Bloomington *Drosophila* Stock Center), and the parent flies were caused to lay eggs for 2 days on the standard diet or the agent diet, and thus, 20 to 50 eggs per vial, of Ser-gal4; UAS-RasG12D, UAS-p53 shRNA, UAS-CycE, UAS-Med shRNA 4-hit flies (non-GFP) were obtained. These eggs were raised at 25° C. for 13 days, and survival rate of the 4-hit flies (non-GFP) raised on each diet was calculated by dividing the number of eclosed individuals by the total number of pupae.

Figure 9:
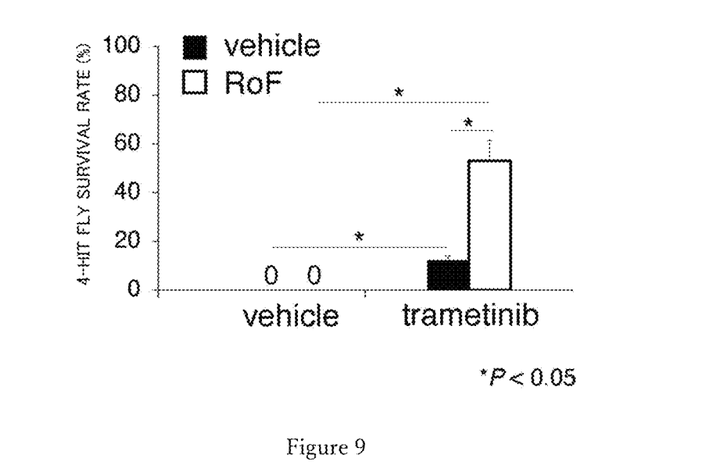
FIG. 9 is a graph illustrating recovery of a survival rate of 4-hit flies through use of both roseoflavin and trametinib.

Results are illustrated in FIG. 9. Trametinib singly improved the survival rate of the 4-hit flies (non-GFP) by about 10%. On the other hand, a combination of trametinib and roseoflavin improved the survival rate by as much as about 50%, and thus it was revealed that a synergic effect for improving the survival rate could be obtained through use of both of these. This reveals that the use of both trametinib and roseoflavin is very effective for preventing or treating pancreatic cancer.

Example 7

A pancreatic cancer suppressing effect through use of both roseoflavin of the RF pathway inhibitor and trametinib of the MEK inhibitor was verified using a pancreatic cancer transplanted mouse.

In the pancreas of each of BALB/cAJcl nu/nu mice, pancreatic cancer cells (AsPC-1) having luciferase gene incorporated therein were transplanted in an amount of $1 \times 10^6$ cells. Luciferin (15 µg luciferin/g of mouse body weight) was administered to the mouse over time, and luciferase activity was measured with IVIS Imaging System. About 2 weeks after the orthotopic transplantation, the mice were divided into the following 4 groups. It is noted that roseoflavin (RoF) was intraperitoneally administered at a dose of 3 mg/kg, and that trametinib (Tr) was orally administered at a dose of 1 mg/kg.

(1) control (a solvent (DMSO) alone administered) (n=7)
(2) roseoflavin (RoF) administered (n=6)
(3) trametinib (Tr) administered (n=5)
(4) roseoflavin (RoF)+trametinib (Tr) both administered (n=5)

Figure 10:
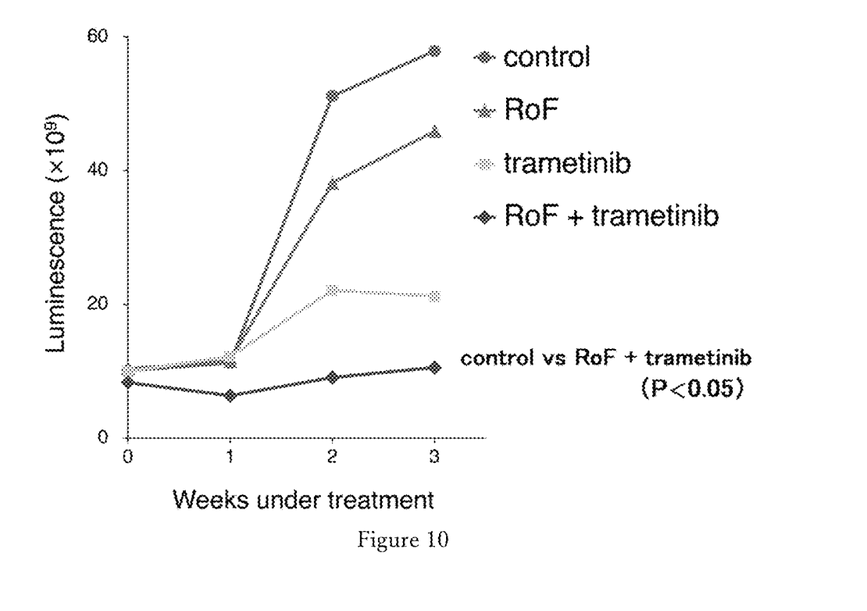
FIG. 10 is a graph illustrating tumor suppression in a mouse having human pancreatic cancer cell orthotopically transplanted therein through use of both roseoflavin and trametinib.

Results are illustrated in FIG. 10. Although trametinib (Tr) singly suppressed tumor growth in the mouse, when roseoflavin (RoF) was combined with trametinib (Tr), the tumor suppressing effect was remarkably improved, and thus, it was revealed that a synergic effect for suppressing tumor could be obtained through use of both of these. This reveals that the use of both trametinib and roseoflavin is very effective for preventing or treating pancreatic cancer.

We claim:

1. A method for treatment of pancreatic cancer comprising administering an effective amount of roseoflavin to a subject.

2. The method according to claim 1, further comprising administering an effective amount of trametinib to the subject.

3. The method of claim 1 wherein the effective amount of roseoflavin is administered alone as a sole pharmaceutically active ingredient.

4. The method of claim 1 wherein the subject is a human.

* * * * *

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 1
tgctgaagca ataaccaccg a                                              21

<210> SEQ ID NO 2
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 2
tcggtggtta ttgcttcagc a                                              21

<210> SEQ ID NO 3
<211> LENGTH: 21
<212> TYPE: DNA
```

```
<213> ORGANISM: Artificial Sequence
<220> FEATURE:
<223> OTHER INFORMATION: synthesized oligonucleotide

<400> SEQUENCE: 3
ttcagtgcga tgaacattgc t                                        21

<210> SEQ ID NO 4
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 4
agcaatgttc atcgcactga a                                        21

<210> SEQ ID NO 5
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 5
tagttatatt caagcata                                            18
```